(12) United States Patent
Albrecht et al.

(10) Patent No.: US 10,274,430 B2
(45) Date of Patent: Apr. 30, 2019

(54) METHODS OF DETERMINING AN ANALYTE CONCENTRATION IN A BODY FLUID SAMPLE, AS WELL AS ANALYTICAL DEVICES AND SYSTEMS FOR USE THEREIN

(71) Applicant: Roche Diabetes Care, Inc., Indianapolis, IN (US)

(72) Inventors: Gertrud Albrecht, Mannheim (DE); Edgar Baumann, Mannheim (DE); Markus Genthner-Riegler, Heidelberg (DE); Stefan Kalveram, Viernheim (DE); Christian Niesporek, Heidelberg (DE); Kai-Oliver Schwenker, Hassloch (DE); Markus Serr, Zug (CH); Frederic Wehowski, Hockenheim (DE); Klaus Wettengel, Flörsheim-Dalsheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 58 days.

(21) Appl. No.: 15/145,840

(22) Filed: May 4, 2016

(65) Prior Publication Data

US 2016/0245755 A1  Aug. 25, 2016

Related U.S. Application Data

(63) Continuation of application No. PCT/EP2014/075780, filed on Nov. 27, 2014.

(30) Foreign Application Priority Data

Nov. 28, 2013  (EP) .................................. 13194791

(51) Int. Cl.
 *G01N 21/75* (2006.01)
 *G01N 33/50* (2006.01)
 (Continued)

(52) U.S. Cl.
 CPC .............. *G01N 21/75* (2013.01); *G01J 3/433* (2013.01); *G01N 21/78* (2013.01);
 (Continued)

(58) Field of Classification Search
 CPC ............ G01J 3/433; G01N 2021/7786; G01N 21/274; G01N 21/4738; G01N 21/75;
 (Continued)

(56) References Cited

U.S. PATENT DOCUMENTS 5,526,120 A   6/1996  Jina et al.
6,055,060 A   4/2000  Bolduan et al.
(Continued)

FOREIGN PATENT DOCUMENTS

| EP | 1912058 A1 | 4/2008 | |
|----|------------|--------|---|
| WO | WO-9923479 A1 * | 5/1999 | ........... G01N 21/255 |
| WO | WO9923479 A1 | 5/1999 | |

*Primary Examiner* — Jennifer Wecker

(57) ABSTRACT

Methods, analytical devices and analytical systems are provided for determining at least one analyte concentration in a body fluid sample. The methods, which may be incorporated into the devices and systems, can include the following steps: applying a body fluid to a test carrier; illuminating the test carrier by at least one light source, where the at least one light source is modulated by using at least two modulation frequencies; receiving light remitted by the test carrier by using at least one detector; determining an analyte concentration by evaluating at least one detector signal generated by the detector, where the detector signal is demodulated with the at least two modulation frequencies to generate at least two demodulated detector signals, each demodulated signal corresponding to one of the modulation frequencies; and detecting a fault by comparing the at least two demodulated detector signals.

18 Claims, 2 Drawing Sheets

(51) Int. Cl.
*G01J 3/433* (2006.01)
*G01N 21/78* (2006.01)
*G01N 21/84* (2006.01)
*G01N 33/487* (2006.01)
*G01N 21/15* (2006.01)
*G01N 21/27* (2006.01)
*G01N 21/47* (2006.01)
*G01N 21/77* (2006.01)

(52) U.S. Cl.
CPC ... *G01N 21/8483* (2013.01); *G01N 33/48707* (2013.01); *G01N 21/274* (2013.01); *G01N 21/4738* (2013.01); *G01N 33/4875* (2013.01); *G01N 2021/7786* (2013.01); *G01N 2201/0612* (2013.01); *G01N 2201/0621* (2013.01); *G01N 2201/0697* (2013.01)

(58) Field of Classification Search
CPC ............... G01N 21/78; G01N 21/8483; G01N 2201/0612; G01N 2201/0621; G01N 2201/0697; G01N 33/4875
See application file for complete search history.

(56) References Cited

U.S. PATENT DOCUMENTS

| | | | |
|---|---|---|---|
| 2003/0169426 A1* | 9/2003 | Peterson | G01N 21/8483 356/446 |
| 2008/0119421 A1* | 5/2008 | Tuszynski | A61K 31/195 514/34 |
| 2008/0259339 A1* | 10/2008 | Wehowski | G01N 21/274 356/434 |
| 2010/0187450 A1* | 7/2010 | Kahlman | G01N 21/552 250/573 |
| 2010/0267049 A1* | 10/2010 | Rutter | G01N 21/6428 435/7.1 |

\* cited by examiner

METHODS OF DETERMINING AN ANALYTE CONCENTRATION IN A BODY FLUID SAMPLE, AS WELL AS ANALYTICAL DEVICES AND SYSTEMS FOR USE THEREIN

CROSS-REFERENCE TO RELATED APPLICATIONS

This patent application is a continuation of Int'l Patent Application No. PCT/EP2014/075780 (filed 27 Nov. 2014), which claims priority to and the benefit of EP Patent Application No. 13194791.3 (filed 28 Nov. 2013). Each patent application is incorporated herein by reference as if set forth in its entirety.

TECHNICAL FIELD

This patent application relates generally to engineering and medical diagnostics, and more particularly, it relates to methods of photometrically measuring an analyte concentration in a body fluid sample that use at least one light source modulated at at least two modulation frequencies, as well as relates to analyte devices and systems for use in such methods.

BACKGROUND

Determining one or more analyte concentrations in a bodily fluid may be performed by photometric/optical measurements. In this manner, a body fluid sample may be applied onto a test carrier, which then is illuminated by light to perform the photometric measurement. Typically, reflective measurements are performed to determine an amount of light elastically or inelastically reflected, scattered, or remitted by the test carrier. In general, such a test carrier uses at least one test chemical (i.e., one or more chemical compounds or chemical mixtures) adapted for performing a detectable reaction, which leads to a detectable change of the test carrier such as, for example, an optical change, especially a color change. The test chemical also may be referred to as a test substance, a test chemistry, a test reagent, a detection reagent, or a detector substance. For details of potential test chemicals and test carriers incorporating such test chemicals, which may be used within the context of the present disclosure, reference is made to Hönes et al. (2008) *Diabetes Technol. Ther.* 10:S10-S26. Other types of test chemicals, test substances and/or test carriers are feasible and may be used in connection with the present disclosure.

By using one or more test chemicals, the detection reaction may be initiated, the course of which depends on the analyte concentration to be determined. Typically, the test chemical is adapted to perform at least one detection reaction when the analyte is present in the body fluid sample, where the extent and/or degree of the detection reaction, such as the kinetics of the detection reaction, depends on the analyte concentration. In case of photometric measurements, the test carrier may be illuminated with light, where the light may be diffusely reflected from the test carrier and detected by an analyzing device. For example, the analyte concentration in a body fluid sample can be determined by measuring the reflectivity of the test carrier when the detection reaction is completed. Additionally or alternatively, the progress of the detection reaction may be monitored by measuring a temporal change of the reflectivity. Thus, in photometric measurements, the test chemical may be adapted to change at least one reflective property (i.e., a color) due to the detection reaction.

Measuring and analyzing remitted light typically imposes some technical challenges. On the one hand, these measurements can involve small currents and/or voltages. Measuring such small currents or voltage, however, is challenging since interferences may occur such as, for example, interferences due to low-frequency voltages. On the other hand, optical disturbances may occur because of ambient light. Thus, when determining the analyte concentration with photometric measurements, analyzing devices and methods are needed that reduce inference of these disturbances.

EP Patent No. 0 632 262 discloses methods of detecting and evaluating analog photometric signals in a test carrier analysis apparatus. The test field of the test carrier is irradiated by a light source that is clocked in light and dark phases. The light and dark phases form an irregular sequence with a frequency spectrum having a large number of different frequencies. The light is reflected and detected by a measurement receiver, and its measured value is passed to a measurement integrating and digitalizing circuit for evaluation, where the irregular signal is filtered out.

Likewise, EP Patent No. 1 912 058 discloses systems adapted for measuring and evaluating optical signals for detecting an analyte in an analysis liquid. The system includes a test carrier and a light source for illuminating an optical evaluation zone of the test carrier. In addition, the systems include two signal sources adapted for generating two control signals, mixed by a mixer unit to generate a light control signal for the light source. A light sensor receives the remitted light and converts it into a measuring signal. Further, the systems include two frequency-selective amplifiers, each receiving the measurement signal and one of the control signals, and an evaluation unit to which the output signal of the frequency-selective amplifiers are fed. In the evaluation unit, the output signals are compared, and information about interference of the measurement by external light is determined from the result of the comparison. When an interference of the measurement is above a certain threshold, the measurement is recognized as faulty and is rejected. Thus, no analyte concentration is provided.

Further, and in many cases, the test carrier must be oriented within the device for determining one or more analyte concentrations such that the device is able to perform the test. For example, US Patent Application Publication No. 2003/0169426 discloses test meters capable of determining the orientation of a test carrier within it. The test carrier has a first major surface and an opposing second major surface. Each major surface includes an orientation indicator region, where the orientation indicator regions differ by at least one optical property such as, for example, reflectance. The test meter includes a test region for accepting a test carrier and also includes an optical orientation sensor. The optical orientation sensor generates an orientation signal indicative of an optical property of the orientation indicator region.

Likewise, U.S. Pat. No. 5,526,120 discloses test carriers and apparatuses where each has an asymmetry. The asymmetries combine to permit a test carrier to be inserted into the apparatus when it is correctly aligned but prevent the test carrier from being fully inserted if it is wrong side up. In addition, the apparatus can detect whether or not the test carrier has been fully inserted.

Despite the advantages implied by the known devices and methods, many technical challenges remain. For example, many known devices and methods are not suited for recognizing disturbances—both internal and external—before or while measuring. For example, internal disturbances have to be considered, such as fluctuations of one or more light sources and/or noise within electronic components of the devices. Further, external disturbances have to be considered, such as disturbances induced by ambient light. Such disturbances may lead to significant faults and falsifications of the measured analyte concentrations.

Known devices and methods, however, allow for fault detecting only at the end of each measurement. For example, paragraph [0047] of EP Patent No. 1 912 058 discloses comparing analytical results that have been determined from raw data of output signals of a frequency-selective amplifier, and not raw data directly. Thus, in case a measurement is rejected, the whole test carrier wetted by the sample is rejected, and a new sample has to be applied on a new test carrier, implying that the new sample has to be taken from a patient or user. Thus, many known devices and methods typically imply a drawback that test carriers are wasted and that the user or patient, at least to some extent, will have to generate repeated body fluid sample to obtain a reliable measurement. Further, and in view of an increased use of modern light sources like energy-saving lamps, light-emitting diodes (LEDs), etc., and in view of an increased trend towards miniaturization of analytical devices, disturbances of photometric measurements may increase. Consequently, a strong need exists for devices and methods that are suited to at least partially avoid waste of test carriers and frequent generation of samples yet still provide fast and reliable measurement results.

Further, EP Patent No. 1 912 058 discloses that a first signal source generates a first control signal with a base frequency and a second signal source generates a second control signal with a frequency that is a multiple of the base frequency. The intensities of the first control signal and the second control signal are different from each other. However, using control signals with different intensities may enhance the possibility of faulty fault detecting in case of low measurement signals because of faultily identifying a low measurement signal and not detecting a disturbance. Thus, even though a valid measurement signal was measured, the valid measurement signal may erroneously be identified as a disturbance rather than as a valid measurement signal.

It is therefore an object of the present disclosure to provide methods and devices for determining an analyte concentration in a body fluid sample that overcome the above-mentioned drawbacks. Moreover, the methods and devices disclosed herein are capable of reliably determining an analyte concentration in a body fluid even in the presence of disturbances.

BRIEF SUMMARY

Methods are provided for determining at least one analyte concentration or presence in a body fluid sample. Briefly, the methods can include steps of a) applying a body fluid sample to a test carrier; b) illuminating the test carrier by using at least one light source, where the at least one light source is modulated by using at least two modulation frequencies; c) receiving light remitted by the test carrier by using at least one detector; d) determining an analyte concentration by evaluating at least one detector signal generated by the at least one detector, where the at least one detector signal is demodulated with the at least two modulation frequencies to generate at least two demodulated detector signals, each demodulated detector signal corresponding to one of the modulation frequencies; and e) detecting a fault by comparing the at least two demodulated detector signals.

In some instances, the methods also include a step of determining at least one dry empty value by evaluating the at least one detector signal generated by the detector before applying the bodily fluid sample to the test carrier.

In view of the foregoing methods, analytical devices are provided that can be used in connection with the methods described herein. The analytical devices can include at least one receptacle for receiving at least one test carrier, where at least one body fluid sample can be applied to the at least one test carrier.

Such devices also can include at least one light source adapted for illuminating the at least one test carrier.

In addition, the devices can include at least one detector adapted for receiving light remitted by the at least one test carrier.

Moreover, the devices can include at least one evaluation unit adapted for determining the at least one analyte concentration by evaluating at least one detector signal generated by the at least one detector.

Furthermore, the devices can include at least one modulation device adapted for modulating the at least one light source by using at least two different modulation frequencies.

The devices also can include at least one demodulation device adapted for demodulating the at least one detector signal with the at least two modulation frequencies to generate at least two demodulated detector signals, each demodulated detector signal corresponding to one of the at least two different modulation frequencies.

The devices also can include at least one fault detection device adapted for detecting a fault by comparing the at least two demodulated detector signals.

In view of such analytical devices, analytical systems are further provided for determining at least one analyte concentration in a body fluid sample, where such analytical systems include an analytical device configured to perform the methods as described herein and at least one test carrier.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
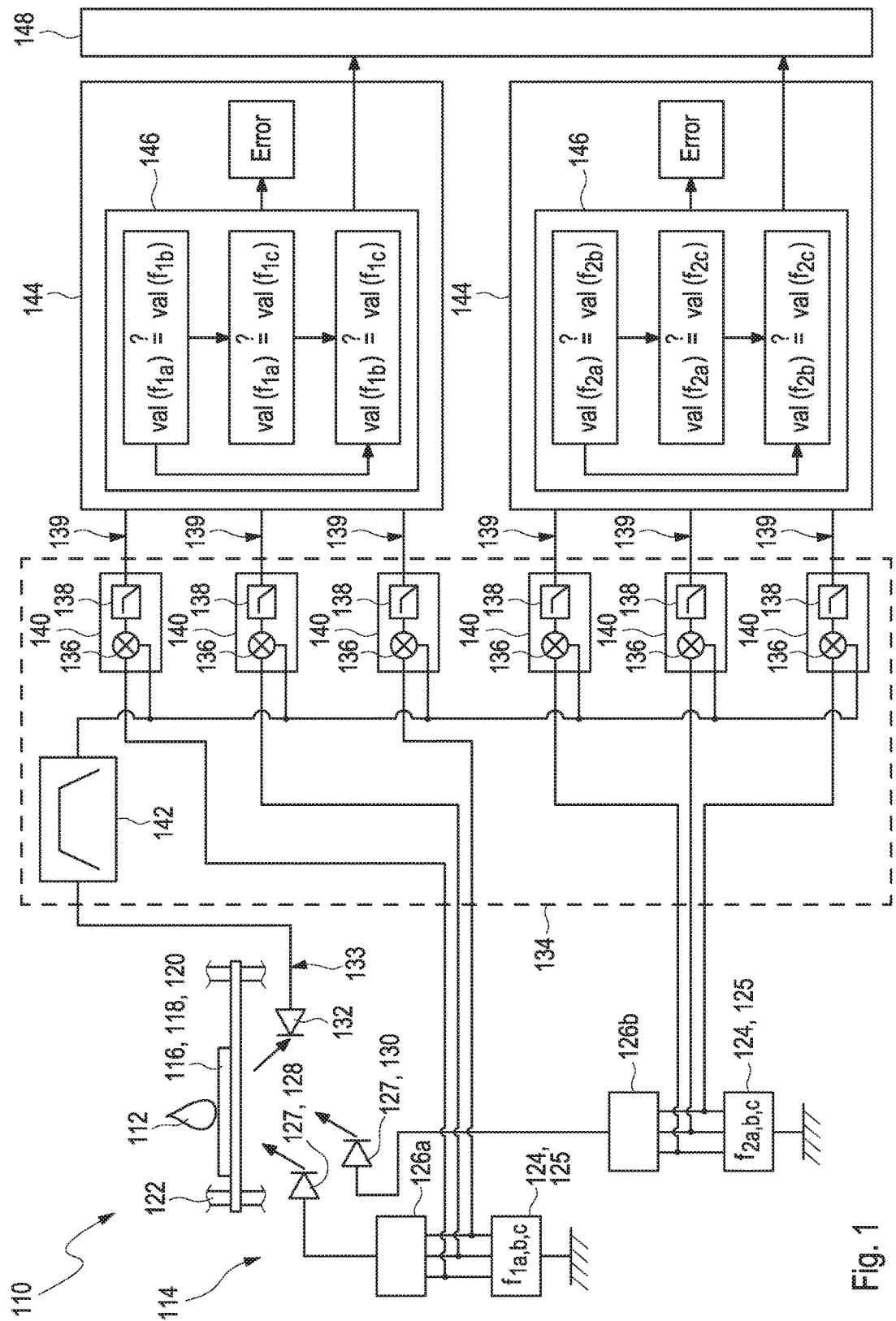
FIG. 1 shows a schematic view of an exemplary embodiment of an analytical system including an exemplary embodiment of an analytical device and a test carrier.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, analytical devices and analytical systems now will be described more fully hereinafter with reference to the accompanying drawings, in which some, but not all embodiments of the inventive concept are shown. Indeed, the methods, analytical devices and analytical systems may be embodied in many different forms and should not be construed as limited to the embodiments set forth herein; rather, these embodiments are provided so that this disclosure will satisfy applicable legal requirements.

Likewise, many modifications and other embodiments of the methods, analytical devices and analytical systems described herein will come to mind to one of skill in the art to which the disclosure pertains having the benefit of the teachings presented in the foregoing descriptions and the associated drawings. Therefore, it is to be understood that the methods, analytical devices and analytical systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, analytical devices and analytical systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

The present disclosure provides methods, analytical devices and analytical systems for determining at least one analyte concentration or presence in a body fluid sample. The methods, devices and systems can be used for determining an analyte concentration such as glucose in one or more body fluid sample types, such as in whole blood. Additionally or alternatively, however, one or more other types of analytes and/or one or more other types of body fluid types may be used. The methods, devices and systems are particularly applicable to the field of diabetes care, both in home monitoring and in hospital applications. Additionally or alternatively, other uses are feasible.

Examples of body fluids that can be used herein include, but are not limited to, blood, especially whole blood; interstitial fluid; saliva; and urine. Additionally or alternatively, other types of body fluids may be used. In some instances, further-processed body fluid such as blood plasma or blood serum may be used.

In general, the analyte may be a substance, a compound, or a combination of substances or compounds present in body fluids. In particular, the analyte may be a substance that is part of a metabolism in a human or animal being or that may take part in the metabolism (e.g., a metabolite). Examples of analytes of interest herein include, but are not limited to, glucose, lactate, triglycerides, ketone, ethanol, total cholesterol, high-density lipoprotein (HDL) cholesterol, low-density lipoprotein (LDL) cholesterol, urea, uric acid, creatinine, and ammonia. Additionally or alternatively, other clinical chemical parameters or analytes of interest include alkaline phosphatase (ALP), creatine kinase (CK), amylase, pancreatic amylase, (gamma)-glutamyltransferase (GGT), glutamic-oxaloacetic transaminase (GOT), glutamic-pyruvic transaminase (GPT), bilirubin, hemoglobin, potassium. Additionally or alternatively, the analytes may be substances or a combination of substances involved in the intrinsic and/or extrinsic coagulation pathway. Generally, the analyte may be any type of clinical parameter of a body fluid that might be of interest for clinical purposes, such as any type of clinical parameter that might be determined from whole blood.

A large number of devices and methods are known for determining one or more analyte concentrations in body fluids. Without restricting the scope of the present disclosure, in the following, reference is mainly made to determining glucose concentrations as an exemplary analyte of interest.

Analytical Devices and Analytical Systems

Prior to, and in connection with, describing the inventive methods below, analytical devices and analytical systems now will be described. To begin, the analytical devices for determining at least one analyte concentration can include at least one receptacle for receiving at least one test carrier. As used herein, "analytical device" means a device adapted to perform at least one analysis for determining one or more analyte concentrations in a body fluid sample. Analytical devices may be hand-held devices or may be stationary or even portable devices. Moreover, the analytical devices are adapted to perform the methods herein. For a description of possible embodiments and definitions, reference can be made to the methods described in detail below.

At least one body fluid sample can be applied to the at least one test carrier. To achieve this aspect, the analytical devices may be adjusted such that the body fluid sample may be applied to the test carrier before inserting the test carrier into the receptacle and/or in a state in which the test carrier is inserted into the receptacle. In the first case, the receptacle may be designed such that the test carrier with the body fluid sample applied thereto may be inserted into the receptacle. In the latter case, the receptacle may be designed such that at least one portion of the test carrier having at least one application position is accessible to a user for applying the sample.

As used herein, "receptacle" means an arbitrarily formed part of the device configured to allow for an insertion of the test carrier. The receptacle may further be adapted to enable applying the body fluid sample to the test carrier. In this manner, the receptacle generally may include at least one means for holding the test carrier in at least one predetermined position. Thus, for example, the receptacle may include one or more of a slot, a guiding structure, a holder, and/or a chamber. Other types of receptacles are feasible. Likewise, the receptacle may be adapted to hold the test carrier in position during the photometric measurement. Moreover, the receptacle may include at least one opening adapted to insert the test carrier into the receptacle, such as one or more of a slotted opening, a rectangular opening, and/or a round opening.

In addition to the above, the analytical devices can include at least one light source adapted for illuminating the at least one test carrier. The light source general may be or may include one or more arbitrary light sources adapted to illuminate the test carrier. As used herein, "light" means electromagnetic waves in one or more of the visible, ultraviolet (UV) and/or infrared spectral ranges, where the visible spectral range can be from about 380 nm to about 780 nm, where the infrared spectral range can be from about 780 nm to about 1 mm, especially from about 780 nm to about 3.0 µm, and where the UV spectral range can be from about 1 nm to about 380 nm, especially from about 50 nm to about 380 nm or even from about 200 nm to about 380 nm. In some instances, the light source is adapted to emit light in the visible spectral range.

As used herein, "about" means within a statistically meaningful range of a value or values including, but not limited to, a stated concentration, length, width, height, angle, weight, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

For example, the light source may be a pulsed light source selected from a LED, a laser (e.g., a laser diode), an incandescent light or other light bulb. Additionally or alternatively, several light sources may be used such as, for example, at least two light sources having differing emission wavelengths and/or having differing spectral properties.

As such, the at least one light source may include at least one first light source being modulated by at least two modulation frequencies and at least one second light source being modulated by at least two modulation frequencies being different from the at least two modulation frequencies by which the first light source is modulated. Thus, it may be possible to illuminate a test carrier and/or carrier track by two light sources. This may be an advantage because an illumination of two different positions on the track carrier indicating a determination of two measurement values may be possible.

In general, when using more than one light source, it may be possible to illuminate one, two, or more different positions. Thus, at least one first light source may be adapted to illuminate at least one first position, and at least one second light source may be adapted to illuminate at least one second position, where the at least one first position and the at least one second position may fully or partially be identical or may fully or partially be non-identical, such as spatially separated and/or overlapping. For example, these different positions may be situated on the same test carrier and/or may be situated on different carrier tracks. Thus, it may be possible to illuminate two or more positions on two or more different test carriers and thus to determine two or more measurement values of two or more different test carriers with the same analytical device. The different test carriers may have different configurations such as a different geometry and/or different optical/photometric properties.

In connection with the at least one light source, the analytical systems also can include at least one detector adapted for receiving light from the at least one light source that is remitted by the at least one test carrier. The detector may be an arbitrary detector configured to receive light and to convert the received light into one or more electric or electronic detector signals.

In this manner, the detector may include at least one light-sensitive element for detecting light propagating from the test carrier to the detector. The detector may generate one or more output detector signals, in particular at least one electronic signal, which may be further evaluated. The detector signal generally may be or may include an analog signal and/or a digital signal. Specifically, the detector signal may include an electric current signal and/or a voltage signal. The at least one detector signal may be a single detector signal or may include a plurality of detectors signals, such as by providing a continuous detector signal including continuously generated detector signals and/or detector signals generated at predetermined points in time and/or at a given detection frequency. The at least one detector signal may be used directly or indirectly in step d), which is described in greater detail below. Thus, the detector signal may be directly processed to determine the analyte concentration.

Additionally or alternatively, one or more preprocessing steps may be applied to the detector signal to transform the detector signal as provided by the detector, also referred to as the raw detector signal or primary detector signal, into one or more secondary detector signals, such as by applying one or more of a filtering and/or an averaging process. In the following, when referring to the detector signal, both the option of using one or more primary detector signals and the option of using one or more secondary detector signals shall be implied.

In some instances, the detector may include at least one light-sensitive element selected from a photodiode; a photomultiplier; and an imaging detector, including a camera chip such as a CMOS and/or a CCD chip. Other light-sensitive elements are feasible.

Moreover, the analytical devices can include at least one evaluation unit adapted for determining the at least one analyte concentration by evaluating at least one detector signal generated by the at least one detector. As used herein, "evaluation unit" means a device or system of multiple devices configured to evaluate the at least one detector signal generated by the at least one detector. For example, the evaluation unit may include a data processing device and/or a computer. In this manner, a microprocessor may be integrated in the evaluation unit. Additionally or alternatively, external data-processing devices may be included into the analytical device, such as one or more personal computers, one or more computer networks, or one or more other types of data processing devices.

Furthermore, the analytical devices can include at least one modulation device adapted for modulating the at least one light source by using at least two different modulation frequencies. As used herein, "modulation device" means a device configured to perform a modulation as defined above.

Thus, the modulation device generally may be adapted to periodically modulate at least one parameter of the at least one light source and/or of the light emitted by the at least one light source.

The signal source may be adapted to generate one or more control signals having at least two modulation frequencies. In particular, the modulation device modulates the light source by using at least three modulation frequencies.

Likewise, the analytical devices can include at least one demodulation device adapted for demodulating the at least one detector signal with the at least two modulation frequencies to generate at least two demodulated detector signals, where each demodulated detector signal corresponds to one of the at least two different modulation frequencies. As used herein, "demodulation device" means a device configured to perform a demodulating process as defined above. Thus, the demodulation device may be adapted to demodulate a signal that was modulated by at least two modulation frequencies. The demodulation device may be adapted such that the demodulation includes independently multiplying the detector signal with the one or more modulation frequencies and filtering the results by using one or more low-pass filters. In addition, the demodulation device may be adapted such that the demodulation, before multiplying the detector signal with the modulation frequencies, includes filtering the detector signal by using at least one band pass filter. In certain instances, the band pass filter is adjustable, manually and/or automatically.

The demodulation device may include at least one lock-in amplifier. For example, the lock-in amplifier may be or may include a single phase lock-in amplifier, which includes a single lock-in-structure using one reference signal. In some instances, the lock-in amplifier may be a digital dual phase lock-in amplifier to be phase independent. The digital dual phase lock-in amplifier may include a dual lock-in-structure, which includes two single lock-in-structures each having a reference signal. A reference signal may have and/or may be modulated with the same modulation frequency by which the light source is modulated. One of the reference signals of the dual lock-in structure may be shifted (e.g., the reference signal may be shifted by about) 90°. An output signal of the dual phase lock-in amplifier may depend on the square root of the sum of the squared individual signals. As used herein, "lock-in amplifier" means a dual phase lock-in amplifier.

Lastly, the analytical devices can include at least one fault detection device adapted for detecting a fault by comparing the at least two demodulated detector signals. The fault detection device is a device or system of devices configured to perform the above described fault detecting. The fault detection device may include a data processing device and/or a computer. The fault detection device may fully or partially be part of the evaluation device and/or may fully or partially be embodied as a separate device. Further, the fault detection device may be adapted to perform the fault detection as an online fault detection, which may be performed permanently or repeatedly. As used herein, "online fault detection" means a fault detection that is performed during a measurement procedure of the optical/photometric measurement, such as during determining the analyte concentration.

For details of potential embodiments of fault detection, reference may be made to the disclosure of the methods as given above and/or as given in further detail below. The fault detection device may be adapted so that comparing the at least two demodulated detector signals includes at least one algorithm selected from a comparison of at least one of the demodulated detector signals with at least another one of the demodulated detector signals; a comparison of at least one of the demodulated detector signals with at least one mean value of the demodulated detector signals; and a comparison of at least one of the demodulated detector signals with at least one threshold value. For example, the fault detection device may be adapted so that when comparing the at least two demodulated detector signals, at least a first one of the demodulated detector signals is compared with at least a second one of the demodulated detector signals and determining that the first demodulated detector signal is faulty in case the first demodulated detector signal deviates from the second demodulated detector signal by more than a predetermined tolerance such as, for example, by a tolerance of about 0-2% or even by a tolerance of about 0-1%.

In general, the fault detection device may be adapted so that the fault detecting includes detecting faulty demodulated detector signals. In some instances, the fault detection device may be adapted so that the fault detecting further includes rejecting the faulty demodulated detector signals and using only non-faulty demodulated detector signals for determining the at least one analyte concentration in the body fluid sample. As used herein, "rejecting" means a process of preventing a further use of a demodulated detector signal that is recognized to be faulty. The rejecting may be an automatic rejecting that automatically prevents using the faulty demodulated detector signal. Additionally or alternatively, the rejecting may be a semi-automatic and/or manual, such as by providing a warning to a user indicating that a specific modulation frequency or demodulated detector signal is faulty.

In particular, the demodulation device may be adapted such that the demodulated detector signals each include a sequence of measurement values, where rejecting the faulty demodulated detector signals may include a rejection algorithm selected from rejecting a current measurement value determined to be faulty; and rejecting the whole sequence of measurement values in case at least one of the measurement values is determined to be faulty. The analytical devices may be adapted such that determining the analyte concentration is aborted in case all of the demodulated detector signals are determined to be faulty. In addition, the analytical devices may be adapted such that in case the determining the analyte concentration is aborted, an output indicating the abortion is issued.

Additional or alternatively, the fault detection device may be adapted so that the fault detecting includes determining a degree of faultiness for the demodulated detector signals determined to be faulty. Likewise, the evaluation unit may be adapted so that at least one faulty demodulated detector signal is used for determining the analyte concentration, where the degree of faultiness is taken into account.

In certain instances, the at least one light source may include at least one first light source being modulated by at least two modulation frequencies and at least one second light source being modulated by at least two modulation frequencies being different from the at least two modulation frequencies by which the first light source is modulated. For each light source at least two signals each with a modulation frequency may be generated by the signal source. In a mixer unit, one control signal for controlling is generated by mixing, in particular adding up, the two signals for each light source. Each of the two light sources may be controlled by one of the generated control signals and may illuminate the test carrier. The remitted light may be detected by a detector. Here, the demodulation device may be adapted so that at least two demodulated detector signals are generated for the modulation frequencies by which the first light source is modulated and where at least two demodulated detector signals are generated for the modulation frequencies by which the second light source is modulated. Hence, the fault detection device may be adapted so that fault detecting is performed both for the demodulated detector signals for the modulation frequencies by which the first light source is modulated and for the demodulated detector signals for the modulation frequencies by which the second light source is modulated.

In other instances, the demodulation device may be adapted so that each of the demodulated detector signals includes a sequence of single measurement values, where the fault detection device may be adapted so that fault detecting is based on comparing the single measurement values. The advantage of comparing single measurement data is that the comparing takes place at an early stage of the measurement and that these measurement data may be available fast as no evaluation steps like calculations and/or integrations are determined.

The fault detection device may be adapted so that fault detecting is performed at least once before applying the body fluid sample to the test carrier. The analytical device may be adapted to determine at least one dry empty value by evaluating the at least one detector signal generated by the detector before applying the body fluid sample to the test carrier. The fault detection device may be adapted so that fault detection is performed at least once during determining the dry empty value. Thus, the fault detecting may be performed before determining the analyte concentration in the body fluid sample. Hence, it may possible to abort the measurement before applying the body fluid sample to the test carrier, so that the inserted test carrier is still usable and not rejected.

As described in detail above, the light source may use at least two frequencies. The described devices and/or system allow reliable measurement results even in case of disturbances. The described devices and/or system are operational even in case of using and/or detecting faulty frequencies.

The analytical devices can be part of an analytical system that includes one or more test carriers. As used herein, "test carrier" means a test element adapted for determining at least one analyte concentration in a body fluid sample. The test carrier may be selected from a test strip, a test tape, a test disc, and an integrated test carrier having at least one test chemical and at least one lancet element. As used herein, "lancet element" means an arbitrary element configured to puncture and/or to cut into the skin of a user to generate at least one body fluid sample. The lancet element may include one or more of a round tip, a sharp tip, a flat tip, a needle and an edge. The lancet element may include further elements such as, for example, elements configured to sample and/or transport the body fluid sample, in particular a capillary.

Test carriers typically include at least one substrate and at least one test chemical directly or indirectly applied to the substrate. In particular, the test carrier may be an optical/photometric test carrier adapted for optically/photometrically determining the analyte concentration or presence. The test carrier generally may have any technically feasible format.

One component for test carriers therefore is the substrate. As used herein, "substrate" means an arbitrarily formed element that can be used as a base for further elements of the test carrier. The form of the substrate may be selected from a strip, a tape, and a disc. Various embodiments are generally feasible and are well known in the art. The test carrier therefore can include at least one substrate and at least one test chemical applied to the substrate, where the test chemical may be adapted to perform at least one detection reaction in the presence of the analyte to be detected and to change at least one optically detectable property due to the detection. The optically detectable property may be an arbitrary optical property that changes due to the detection reaction and, the measurement of which may therefor provide at least one item of information regarding a progress, an extent or a status of the detection reaction. In some instances, the at least one optically detectable information is selected from a color; and a reflection property such as a remission and a fluorescence of the test chemical. Other embodiments are feasible.

The substrate may be a single-layer setup or may be a multi-layer setup. Thus, the substrate may include one or more layers of a paper material, a plastic material such as a foil, a metal, and/or a ceramic material. In addition, combinations of materials are feasible. When the substrate has a multi-layer setup, it can be a laminate. Further, the substrate may include one or more fluidic structures. For this purpose, two or more substrates may be provided, where a channel is disposed in between the substrates, such as by separating the substrates by one or more spacers. Additionally or alternatively, one or more fluidic structures on a surface of the substrate may be provided, such as by using one or more open capillary channels, such as one or more capillary slits. Various embodiments are feasible and are well known in the art.

In addition to the substrate, the test carrier can include one or more test chemicals that directly or indirectly may be contacted with the body fluid sample. For potential embodiments of the at least one test chemical, reference may be made to the disclosure of potential test chemicals provided elsewhere herein. In some instances, the test carrier may include one or more test fields having one or more continuous or discontinuous detection layers that incorporate at least one test chemical.

The at least one test chemical typically forms at least one test field and/or is part of at least one test field. The test field may be a single-layer setup, having only one detection layer of the test chemical. Alternatively, the test field may have a multi-layer setup of at least two layers, where at least one detection layer of the at least one test chemical may be combined with one or more additional layers, such as one or more spreading layers and/or one or more separation layers and/or one or more pigment layers for providing an optical background, such as a white background, for improved optical measurements. Multi-layer setups of this type are well known in the art. Thus, for example, the test field may include at least one detection layer and, additionally, at least one separation layer (e.g., for separating blood cells) and/or at least one optical layer having one or more pigments, such as one or more inorganic pigments, such as one or more metal oxides (e.g., titanium dioxide ($TiO_2$)).

For details of potential test chemicals that may be used herein, reference may be made to Hönes et al. (2008), supra; as well as to Int'l Patent Application Publication Nos. WO 2010/094426, WO 2010/094427, WO 2007/012494, WO 2009/103540, WO 2011/012269, WO 2011/012270, and WO 2011/012271 (which also is referred to as the cNAD test substance). Further, reference may be made to EP Patent Application Publication Nos. 0 354 441, 0 431 456, 0 302 287, 0 547 710, and 1 593 434. Other types of test carriers and/or test substances are feasible and may be used in connection with the present disclosure.

Besides the substrate and one or more test chemicals, test carriers may include at least one application location, where a body fluid sample may be applied thereto. Consequently, the at least one application location may be a location in which a sample of the body fluid is applicable to the test carrier. In general the test carrier may include a plurality of application locations.

Moreover, the test carrier can include one or more additional layers such as, for example, one or more reflective layers having one or more colored pigments such as white pigments and/or one or more separation layers adapted for separating off one or more components of the body fluid sample such as one or more cellular components. Other embodiments are feasible.

The test carrier generally may have an arbitrary form or format, such as one or more of the test carrier formats known in the art. For example, the test carrier may be selected from a test strip, a test tape, a test disc, and an integrated test carrier having at least one test chemical and at least one lancet element.

Such test carriers therefore can be incorporated into and used in connection with the analytical devices described above to form the analytical system.

In view of the above description of the analytical devices and systems, FIG. 1 depicts a schematic view of an analytical system 110 for determining at least one analyte concentration in a body fluid 112. The analytical system 110 includes an analytical device 114 and a test carrier 116, which in this exemplary embodiment is embodied as a test strip. The test carrier 116 may include at least one substrate 118 and at least one test chemical 120, which can be applied to and/or integrated into the substrate 118. The test chemical 120 is adapted to change at least one optically detectable property due to a detection reaction. The analytical device 114 includes a receptacle 122 in which the test carrier 116 may be inserted.

In addition, the analytical device 114 may include at least one, especially two or more, modulation devices 124. Each of the modulation devices 124 may include at least one signal source 125, where each signal source 125 can generate a different set of control signals, such as three or more control signals, having different modulation frequencies, such as having three or more different modulation frequencies.

In FIG. 1, the three modulation frequencies of the three control signals of the first modulation device 124 are denoted by f1a, f1b and f1c, whereas the three modulation frequencies of the three control signals of the second modulation device 124 are denoted by f2a, f2b and f2c.

For further reference, devices and processes concerning the first set of frequencies may be referred to as a first channel, whereas devices, frequencies and processes concerning the second set of frequencies may be referred to as a second channel.

The analytical device may further include two or more mixer units 126. For potential details of the mixer units 126, reference may be made to EP Patent No. 1 912 058. Control signals generated by the first channel may be transferred into a mixer unit 126a, and the control signal of the second channel may be transferred into another mixer unit 126b. In both of the channels, a control signal may be generated by mixing the three control signals in the mixer unit 126.

Moreover, the analytical device 114 includes at least one light source 127. As shown in FIG. 1, the light source 127 can be a first light source 128 and a second light source 130. The first light source 128 may be controlled by the control signal of the first channel, whereas the second light source 130 may be controlled by the control signal of the second channel. In this manner, the test carrier 116 can be illuminated by the light originating from the first light source 128 and the second light source 130. The test carrier 116 remits the light that then is detected by a detector 132. The detector 132 may convert the light signals into an electronic signal that also is referred to as a detector signal and is symbolically referred to by reference number 133 in FIG. 1. In this embodiment, the detector signal 133 is modulated by six modulation frequencies.

Furthermore, the analytical device includes at least one demodulation device 134 adapted for demodulating the signal of the detector 132. The demodulation device 134 as shown in FIG. 1 may include three multiplication devices 136 and three low pass filters 138 for each of the two channels. In each of the multiplication devices 136, the detector signal may be multiplied or mixed with one of the modulation frequencies, where each of the modulation frequencies is only used once. In each of the low-pass filters 138, the result of the previous multiplication may be filtered. Thus, at output ports of the respective low-pass filters 138, demodulated detector signals may be provided, which are denoted in FIG. 1 by reference numbers 139. In an alternative nomenclature, each of the outputs providing the demodulated detector signals 139 may form a channel of the demodulation device 134.

In addition, FIG. 1 shows that one of the multiplication devices 136, in combination with one of the low-pass filters 138, can be realized as a lock-in amplifier 140. The demodulation device 134 may further include a band pass filter 142 configured to filter the detector signal before passing the detector signal to one or more lock-in amplifiers 140.

The analytical device 114 further includes, for each of the two channels, a fault detection device 144 configured to detect a fault. The fault detection device 144 may be adapted for performing a comparison procedure, which in FIG. 1 is symbolically denoted by reference number 146. During the comparison procedure 146, the demodulated detector signals 139, indicated as val (f1a, f1b, f1c) and val (f2a, f2b, f2c), may be compared. For example in the first channel, in case one of the demodulated detector signal of val (f1a), val (f1b) and val (f1c) differs more than a certain threshold from the other demodulated detector signals, the demodulated detector signal of the respective susceptible frequency may be rejected from further evaluation. As long as two demodulated detector signals are equal at least within a predetermined or adjustable tolerance, an average value may be calculated from these demodulated detector signals for further evaluation. If all demodulated detector signals differ from each other by more than a predetermined or adjustable threshold, an error value may be issued and/or a photometric measurement may be restarted with a new set of frequencies. The comparison process 146 may be performed with the data processing device and/or a computer.

The fault detection may be performed as an online fault detection. Thus, the fault detection may be performed repeatedly or permanently during the photometric measurement. In addition, the fault detection may be performed before applying the body fluid sample 112 to the test carrier 116 (e.g., during a determination of a dry empty value).

Likewise, the analytical device 114 includes an evaluation unit 148 adapted for determining the analyte concentration by evaluating an input of the fault detection device 144 of each of the two channels. In the evaluation unit 148, the analyte concentration determined in the two channels may be compared, and an error value may be issued if the determined values differ from each other more than a certain threshold. For details of the evaluation unit 148, reference may be made to the disclosure given above and/or to the prior art documents as cited above.

Figure 2:
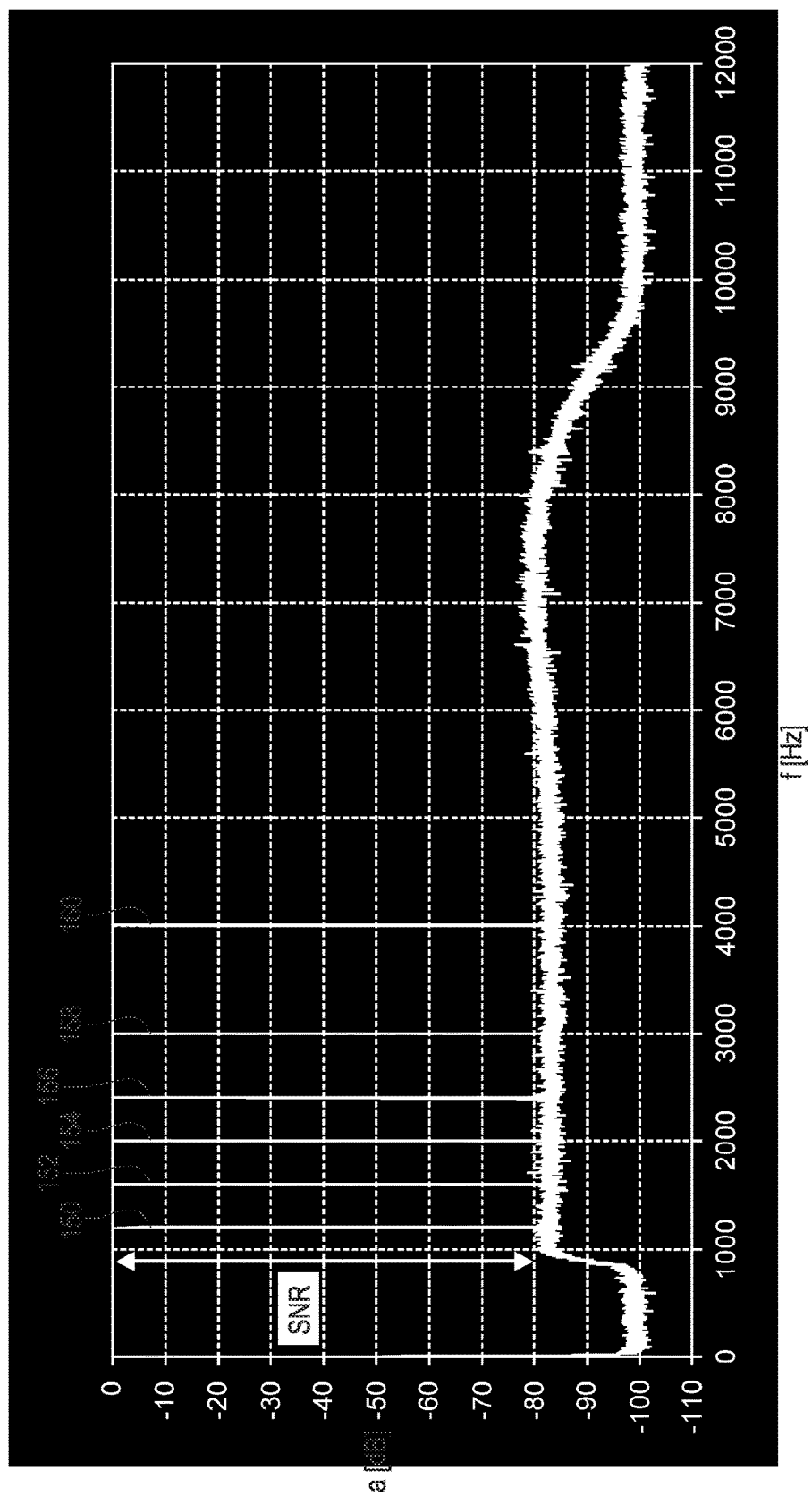
FIG. 2 shows an exemplary embodiment of a signal generated by a detector.

FIG. 2 depicts an exemplary embodiment of a detector signal 133 of the detector 132. A dependency of the frequency f [Hz] over the attenuation a [dB] is depicted. The signal 133 may include, for example, six modulation frequencies 150, 152, 154, 156, 158 and 160. The signal 133 may be determined by the detector 132 before demodulation by the demodulation device 136 and before determining a measurement result by the evaluation unit 148. The signal 133 may include no disturbances. The used six modulation frequencies 150, 152, 154, 156, 158 and 160 may have equal strength. In addition, a signal to noise ratio SNR of the signal 133 is shown. The SNR may be large enough to differentiate each of the modulation frequencies 150, 152, 154, 156, 158 and 160 from noise of the detector 132.

Methods

Having described the analytical devices and analytical system, the analytic determining methods now will be described. The methods can include the steps described herein, and these steps may be, but not necessarily, carried out in the sequence as described. Other sequences, however, also are conceivable.

Furthermore, individual or multiple steps may be carried out either in parallel and/or overlapping in time and/or individually or in multiply repeated steps. Moreover, the methods may include additional, unspecified steps.

For example, the steps may be performed in the given order such as, for example, in the order a)-b)-c)-d)-e). However, other orders of the steps are feasible, such as b)-a)-c)-d)-e). Moreover, one or more of the steps may be performed in parallel and/or in a timely overlapping fashion, such as by performing steps a) and b) at least partially simultaneously and/or by performing steps b), c), d) and e) at least partially simultaneously. Furthermore, one or more of the steps may be performed repeatedly. Thus, and as an example, steps b) and/or c) may be performed repeatedly, such as by performing steps b) and/or c) at least once before step a) and performing steps b), c) and/or e) at least once after performing step a).

Briefly, the methods can include the steps of a) obtaining and applying a body fluid sample to a test carrier; b) illuminating the test carrier by using at least one light source, where the at least one light source is modulated by using at least two different modulation frequencies; c) receiving light remitted by the test carrier by using at least one detector; d) determining an analyte concentration by evaluating at least one detector signal generated by the at least one detector, where the at least one detector signal is demodulated with the at least two modulation frequencies to generate at least two demodulated detector signals, each demodulated detector signal corresponding to one of the modulation frequencies; and e) detecting a fault in the method by comparing the at least two demodulated detector signals.

As noted above, the methods therefore can begin by step a), which includes obtaining and applying a body fluid sample to a test carrier. As used herein, "applying a body fluid sample to a test carrier" means bringing the test carrier in contact with the body fluid sample in any technically feasible way. The applying may take place manually or automatically, such as by applying the body fluid sample to at least one application position. The body fluid sample may be applied to a test chemical of the test carrier, such as a test field including at least one test chemical. Additionally or alternatively, the body fluid sample may be applied to a different application position, such as to an opening of a capillary element adapted to transport the body fluid sample to the test chemical by capillary forces. The applying may take place before, during or after inserting the test carrier into a receptacle of an analytical device adapted for performing the methods described herein. Generally, means and devices for applying the body fluid sample to the test carrier are known in the art.

In step b), the at least one light source is modulated by using at least two modulation frequencies. A modulation of the light specifically may be or may imply a periodical change of at least one parameter of the light, such as at least one parameter selected from an amplitude, a frequency, and a phase. As used herein, "modulation frequency of a modulation" means the frequency of the periodical change of the at least one parameter. Thus, mathematically speaking, the modulation may be a multiplication of the parameter to be modulated with a periodic function, such as one or more of the following functions:

$$a \cdot \exp[-i2\pi ft + \varphi],$$

$$a \cdot \sin[-2\pi ft + \varphi], \text{ and/or}$$

$$a \cdot \cos[-2\pi ft + \varphi],$$

where "a" denotes an amplitude of the modulation, where "f" denotes a frequency of the modulation, and where "$\varphi$" denotes a phase of the modulation. Additionally or alternatively, the parameter to be modulated may be multiplied with a periodic delta function and/or may be multiplied with a periodic pulse function such as a rectangular function. Other types of modulation are feasible.

A modulation with at least two modulation frequencies, such as f1 and f2, generally refers to a doubling of the above-mentioned multiplication (i.e., a repeated modulation with two or more modulation frequencies).

The number of frequencies and/or of possible detection channels working in parallel may be limited by a processing power, such as an installed processing power, and/or by a required energy for mathematical calculation and processing. For a battery-driven analytical device, for instance, such as a battery-driven handheld meter, three frequencies per light source may be used. However, embodiments with more frequencies are feasible, such as for analytical devices connected to an external energy source.

The modulation frequencies may originate from a signal source, which may generate two or more control signals with two or more different frequencies and which may be used as modulation frequencies for modulation and/or a demodulation. For example, the same signal source may be used for generating modulation frequencies both for the modulation and for demodulation. Generally, the modulation frequencies for modulation may be identical to the modulation frequencies of the demodulation. In general, the signal source may be a signal generator, which generates a signal selected from a sinusoidal signal; a rectangular signal; a trapezoidal signal; and/or a delta signal, especially a periodic delta signal. In an optional mixer unit, one control signal, for controlling the pulsed light source, may be generated by mixing these two control signals. The test carrier may be illuminated by this modulated light signal.

The control signals may have equal strength. As used herein, "strength" means an intensity level and/or amplitude level of a signal. The strength of the control signals may be equal to a strength of the detector signal. Thus, the probability of a faulty fault detection in case of low detector signals may be reduced.

In step c), light remitted by the test carrier is received by at least one detector to generate at least one detector signal.

As used herein, "remitted light" means light reflected by the test carrier, especially by the at least one test chemical or at least one test field including the test chemical. The reflection may take place in a diffusive way. Generally, the reflection may fully or partially be elastic and/or inelastic.

In some instances, the step is performed so that an angle of incidence of the illuminating light in the previous step differs from an angle of inspection in this step so that a direct reflection of light at least partially is excluded. A remission measurement may be performed by illuminating the test carrier and/or a part thereof, and by detecting the reflected and/or scattered light from the test carrier By performing this measurement, color changes in the test chemical on the test carrier, which may occur due to a progress of the detection reaction, may be detected. As a result of step c), a remission signal may be generated, such as a relative remission, as will be outlined in further detail below and as generally known in the art of optical detection.

In step d), the analyte concentration is determined by evaluating the at least one detector signal generated by the at least one detector. As will be outlined in further detail below, the evaluation may be performed automatically by using at least one evaluation algorithm in connection with at least one data processing device adapted for automatically performing the evaluation algorithm, such as by using at least one software program.

As used herein, "demodulation" means an inverse process when compared to modulation. Thus, for example, a demodulation may imply multiplying or mixing the modulated function with a periodic function having a specific frequency, which also is referred to as the modulation frequency. Further, demodulation may imply filtering or suppressing high-frequency components after performing the multiplication and/or mixing to obtain low frequency components. For the first process, an electronic mixer or multiplier may be used, multiplying the signal to be demodulated with the at least one demodulation frequency, and for the latter process, a low-pass filter may be used. Thus, generally, demodulation may imply a shifting or change of the signal from the original frequency of the light signal to a frequency that is evaluable and analyzable for detecting one or more faults. The at least one light source may be modulated and/or demodulated by using two or more modulation frequencies.

The detector signal can be demodulated with the at least two modulation frequencies to generate at least two demodulated detector signals, each demodulated detector signal corresponding to one of the modulation frequencies.

The process of demodulation can be understood as extracting the demodulated light signals from the detector signals. In the above-mentioned embodiment, where two light sources, each modulated by two modulation frequencies, may be used, the at least two demodulated detector signals may be generated for the modulation frequencies by which the first light source is modulated and at least two demodulated detector signals may be generated for the modulation frequencies by which the second light source is modulated.

The demodulation may include independently multiplying the detector signal with the modulation frequencies and filtering the results by using low-pass filters. A low-pass filter may be understood as an electronic component which is configured to pass signals with frequencies lower than a cutoff frequency, and to attenuate or suppress signals with higher frequencies.

The demodulation, before multiplying the detector signal with the modulation frequencies, may further include filtering the detector signal by using at least one band pass filter. As used herein, "band pass filter" means an electronic device configured to allow frequencies within a certain, predetermined range to pass and to reject other frequencies outside this range. The band pass filter may be adjustable. Thus, it may be possible to adjust the pass band to the used frequencies in the measurement.

In connection with step d), step e) includes detecting one or more faults by comparing at least two demodulated detector signals. The fault detecting may be understood as recognizing disturbances, in particular disturbances due to one or more of ambient light, disturbances of one or more of the light sources and disturbances of one or more electronic components. Other disturbances are feasible. As used herein, "detecting one or more faults by comparing at least two demodulated detector signals" means a fault detecting that takes into account the comparison by any suitable means, such as by implementing one result of the comparison into a fault detection algorithm as a variable and/or as a parameter. Thus, for example, and as will be outlined in further detail below, the fault detecting may imply comparing one or more variables with at least one threshold, where the one or more variables may imply at least one result of the comparison.

Further, the fault detecting may provide a possibility to determine a reliable measurement value of an optical/photometric measurement in presence of ambient light and/or rejecting the measurement. The fault detecting may be an online fault detection that is performed permanently or repeatedly. The fault detecting, however, may be repeated once or several times during the optical/photometric measurement.

In some instances, the fault detecting is based on comparing at least two demodulated detector signals. Generally, as used herein, "comparing at least two demodulated detector signals" means using an algorithm adapted to generate a comparison result that depends on the magnitude of each of the demodulated detector signals and/or that depends on forming differences of two normed demodulated detector signals. Thus, for example, the comparing may imply forming a difference between the at least two demodulated detector signals and/or may imply forming a quotient of the at least two demodulated detector signals. In case the demodulated detector signals each include a series of single values, the comparing may imply comparing a current or present value of the series. The comparison, for example, may include at least one algorithm selected from a comparison of at least one of the demodulated detector signals with at least another one of the demodulated detector signals; a comparison of at least one of the demodulated detector signals with at least one mean value of the demodulated detector signals; and/or a comparison of at least one of the demodulated detector signals with at least one threshold value. Thus, generally, demodulated detector signals may be compared directly with each other or may be compared with at least one representative value representing a normal condition and/or representing the entity of the demodulated detector signals.

Generally, and as outlined above, the fault detecting may imply at least one threshold comparison. Thus, as an example, one or more of the demodulated detector signals and/or a difference between at least two demodulated detector signals and/or a quotient of two or more detector signals may directly or indirectly be compared to one or more thresholds.

Additionally, the fault detecting may include detecting faulty demodulated detector signals. A demodulated detector signal may be recognized as faulty, if the at least two generated demodulated detector signals show discrepancies of more than a predetermined tolerance. In some instances, more than two modulation frequencies may be used such as, for example, three. Thus, one of the three demodulated detector signals may be recognized as faulty if it differs from the other two demodulated detector signals by more than a predetermined tolerance, whereas the two other demodulated detector signals show similar values. If all demodulated detector signals differ by more than a predetermined tolerance, the whole set of demodulated signals may be detected as faulty.

The comparing of at least two demodulated detector signals may include comparing at least a first one of the demodulated detector signals with at least a second one of the demodulated detector signals and determining that the first demodulated detector signal is faulty in case the first demodulated detector signal deviates from the second demodulated detector signal by more than a predetermined tolerance such as, for example, by a tolerance of about 0-2% or even by a tolerance of about 0-1%.

Further the fault detecting may include rejecting demodulated detector signals that are recognized as faulty demodulated detector signals, and may imply using only non-faulty demodulated detector signals for determining the at least one analyte concentration in the body fluid sample. If one of the demodulated detector signals is detected as faulty, this demodulated detector signal is rejected for determining the at least one analyte concentration in the body fluid sample. If the whole set of the demodulated detector signals are detected as faulty, the measurement is repeated with a new set of frequencies. In the latter case, the change of the set of frequencies may result in a certain settling time of the analysis devices (e.g., the band pass filters). The demodulated detector signals each may be a sequence of measurement values, where rejecting the faulty demodulated detector signals may include a rejection algorithm selected from rejecting a current measurement value that is determined to be faulty; and/or rejecting the whole sequence of measurement values in case at least one of the measurement values is determined to be faulty. In some instances, the method may be aborted in case all of the demodulated detector signals are determined to be faulty. Further, each of the demodulated detector signals may include a sequence of single measurement values, where the fault detection may be based on comparing the single measurement values. As used herein, "single measurement value" means raw, non-evaluated and/or non-analyzed data. For example, single measurement values are issued by the detector about every 20 ms or even about every 10 ms.

Additionally or alternatively, the fault detecting may include detecting faulty demodulated detector signals. The fault detecting also may include determining a degree of faultiness for the demodulated detector signals that are determined to be faulty. Thus, it is possible that the at least one faulty demodulated detector signal may be used for determining the at least one analyte concentration, where the degree of faultiness is taken into account.

The methods can be performed repeatedly, where, in case in one of the repetitions of the method a faulty demodulated detector signal is found for a specific modulation frequency, the modulation frequency may be not used in a subsequent repetition of the method. In general, it is possible to change, in case a faulty demodulated detector signal is found for a specific modulation frequency, to another frequency not used so far. However, then settling times will occur.

When two or more light sources, each modulated by at least two modulation frequencies, the fault detection may be performed both for the demodulated detector signals for the modulation frequencies by which the first light source is modulated and for the demodulated detector signals for the modulation frequencies by which the second light source is modulated. Thus, for example, a reliable measurement value of the at least one analyte concentration may be possible, even if in one set of demodulation frequencies for the modulation frequencies by which a light source, selected from the first and the second light source, is modulated one or more demodulated detector signals are detected as faulty, and if in the other set of demodulation frequencies for the modulation frequencies by which the other light source, selected from the group of the first and the second light source, is modulated no faulty demodulated detector signal has been detected, by using only the light of the non-faulty light source.

In some instances, the fault detecting may be performed at least once before applying the body fluid sample to the test carrier.

As noted above, further steps may be performed before, during, and/or after steps a)-e). Further, and in certain embodiments, additional steps may be performed even without using the test carrier. Thus, as outlined in further detail below, it may be possible to perform an ambient light fault detecting step and/or a determining a dry empty value and/or a position verifying step before performing steps a)-e). Thus, in case the optional ambient light fault detection step should reveal that the ambient light does not allow for an analyte measurement (such as in case an ambient light level, at least at certain modulation frequencies, should be above a tolerance threshold), the measurement may be aborted, without subsequently performing the sample applying step. Additionally or alternatively, in case the determining of at least one dry empty value concludes that the test carrier is unusable, such as due to aging or deterioration effects, the measurement may be aborted, without subsequently performing the sample applying step. Similarly, in case the position verifying step should reveal that the test carrier is misplaced or not aligned properly, the measurement may be aborted, without subsequently performing the sample applying step.

Thus, the methods may further include determining at least one dry empty value by evaluating the at least one detector signal generated by the detector before applying the bodily fluid sample to the test carrier. Performing a remission measurement of the test carrier before applying the body fluid sample, the so-called dry empty value, is well known in the art. The fault detecting may be performed at least once during determining the dry empty value, and the dry empty value may be compared to reference values to determine a usability of the test carrier. In case the usability of the test carrier may be limited due to defects (e.g., aging defects caused by environmental influences such as humidity, light or temperature), it may be possible to reject the test carrier before applying the body fluid sample to the test carrier and/or to adjust measurement values (e.g., one or more of the at least one detector signal and the determined analyte concentration).

Additionally or alternatively, the methods further may include at least one position-verifying step, where the position-verifying step may include the following:
   i. inserting the test carrier into the analytical device;
   ii. illuminating the test carrier by the at least one light source;

iii. receiving light remitted by the test carrier by using the at least one detector; and iv. determining at least one position of the test carrier within the analytical device by evaluating at least one detector signal generated by the detector, where the position includes at least one of a location and/or an orientation of the test carrier.

These steps may be performed in the given order such as, for example, i)-ii)-iii)-iv). However, other orders for the steps are feasible such as, for example, ii)-i)-iii)-iv). Thus, as an example, the test carrier may be or may include a strip-shaped test carrier or a test tape that may be inserted into a receptacle of the analytical device, before illuminating the test carrier by the at least one light source. Additionally or alternatively, the test carrier, such as a test tape and/or a test strip, may include one or more of at least one marking, at least one coating and/or at least one other item of information. The at least one item of information may contain at least one visually detectable item of information that may be detected by the at least one analytical device. The at least one item of information may contain at least one item of information regarding an appropriate use of the test carrier, such as at least one calibration information, and/or may contain at least one other item of information, such as a positioning mark or fiducial mark.

The analytical devices may be adapted for reading the at least one item of information, such as during insertion of the test carrier into the analytical device and/or within the analytical device. The analytical devices may further be adapted for evaluating the at least one item of information and/or for controlling at least one process according to the at least one item of information. Thus, the analytical devices may be adapted for controlling a positioning of the test carrier and/or for detecting whether the test carrier is correctly positioned. For example, the analytical devices may be adapted for illuminating a test tape and for detecting at least one marking on the test tape and/or for detecting at least one test field on the test tape to control the positioning of the test tape and/or to detect whether the test tape is correctly positioned. A controlling of the positioning of the test tape may be performed by controlling an appropriate feeding mechanism of the analytical devices, such as by controlling a motor for positioning the test tape. Thus, specifically in the latter case, an illumination of the test carrier may take place before or during insertion of the test carrier into the analytical device, such as for the purpose of monitoring the insertion process itself, such as a positioning process.

Further, one or more of the steps may be performed in parallel and/or in a timely overlapping fashion, such as by performing steps i) and ii) at least partially simultaneously and/or by performing method steps ii), iii) and iv) at least partially simultaneously. Further, one or more of the steps may be performed repeatedly. Thus, for example, steps ii) and/or iii) may be performed repeatedly. Further, additional steps may be present that are not listed.

The test carrier may be inserted into a receptacle of the analytical device. The test carrier and/or the analytical device and/or the light source and/or the detector specifically may be identical to the respective devices used in steps a)-e). Additionally or alternatively, however, at least one additional light source and/or at least one additional detector is dedicated to the position-verifying step. For a description of possible embodiments and definitions of these devices, reference can be made to the above-mentioned devices used in steps a)-e) and the above-mentioned analytical devices. In general, other configurations of these devices may be possible.

The position-verifying step may be performed before performing steps a)-e). The position-verifying step may include determining the location and/or orientation of test carrier, including the possibility of determining a location or position of a part thereof such as a location or position of at least one test field of the test carrier, within the analytical device. As outlined above, steps i)-iv) may be performed at least once before applying the body fluid sample to the test carrier, such as before performing the combination of steps a)-e). In this embodiment, steps i)-iv) may be performed at least once before applying the body fluid sample to the test carrier to determine at least one position of the test carrier within the analytical device. The test carrier and/or the test field of the carrier may include a marking (e.g., a color marking) and/or another arbitrary marking with a known remission. As used herein, "position" means a location and/or orientation of the test carrier or a part thereof, such as of at least one test field of the test carrier, and/or the marking of the test carrier within the analytical device (e.g., within the receptacle of the analytical device). The remission of light of the test carrier may depend on its position within the analytical device. A proper alignment within the analytical device may be required for reliable measurement values.

After performing steps i)-iv), the determined measurement values (e.g., one or more of the at least one detector signal and the determined analyte concentration) may be compared to reference values. In case the test carrier is aligned properly, the determined measurement values may correspond, within specified limits (such as within one or more thresholds) to the reference values.

Determining of the position may be performed once before applying the body fluid sample to the test carrier and/or during the photometric measurement. Hence, in case the test carrier is not aligned properly within the analytical device, it may be possible to abort the measurement at any desired time (e.g., before applying the body fluid sample to the test carrier) and/or to adjust measurement values (e.g., one or more of the at least one detector signal and the determined analyte concentration). In case it is determined that the test carrier is not aligned properly within the analytical device, an alignment may be performed by a user and/or automatically. Further in case at least one or more of the modulation frequencies may be susceptible, the susceptible modulation frequency may not be considered for the evaluation of the analyte concentration and/or a set of frequencies may be changed.

Further, the fault detecting may be performed at least once while determining the position of the test carrier.

In some instances, an ambient light fault detecting step may be performed without using a test carrier. Herein, the method further may include at least one ambient light fault detecting step, where the ambient light fault detecting step may include the following:

I. receiving ambient light by using the at least one detector;

II. evaluating at least one detector signal generated by the detector; and

III. performing an ambient light fault detection by comparing the at least one detector signal generated by the detector with the modulation frequencies.

These steps may be performed in the given order such as, for example, I.-II.-III. However, other orders of the steps are feasible such as, for example, II.-I.-III. Further, one or more of the steps may be performed in parallel and/or in a timely overlapping fashion, such as by performing steps I. and II. at least partially simultaneously. Further, one or more of the steps may be performed repeatedly. Further, additional steps may be present that are not listed.

In other instances, the ambient light detecting may be performed after inserting the test carrier into the analytical device. Herein, the method further may include at least one ambient light fault detecting step, where the ambient light fault detecting step may include the following:

I'. inserting the test carrier into the analytical device;
II'. illuminating the test carrier by the at least one light source;
III'. receiving ambient light by using the at least one detector;
IV'. evaluating at least one detector signal generated by the detector; and
V'. performing an ambient light fault detection by comparing the at least one detector signal generated by the detector with the modulation frequencies.

These steps may be performed in the given order such as, for example, I'.-II'.-III'.-IV'.-V'. However, other orders of the steps are feasible such as, for example, II'.-I'.-III'.-IV'.-V'. Further, one or more of the steps may be performed in parallel and/or in a timely overlapping fashion, such as by performing steps I'. and II'. at least partially simultaneously and/or by performing steps II'., III'. and IV'. at least partially simultaneously. Further, one or more of the steps may be performed repeatedly. Thus, for example, steps II'. and/or III'. may be performed repeatedly. Further, additional steps may be present that are not listed.

In certain instances, a first ambient light fault detecting step may be performed before inserting a test carrier into the analytical device and a second ambient light fault detecting step may be performed after inserting a test carrier into the analytical device.

In all of these instances, the ambient light fault detecting step may be based on comparing at least one detector signal with the modulation frequencies. As used herein, and when referring to the modulation frequencies in the context of the ambient light fault detecting and comparing at least one detector signal with the modulation frequencies, "modulation frequencies" mean those frequency components of the detector signal at the respective modulation frequencies. Thus, a full or partial frequency analysis of the at least one detector signal may be performed, thereby deriving frequency components of the detector signal and, specifically, deriving frequency components of the detector signal at the modulation frequencies. Consequently, and as used herein, "comparing the at least one detector signal generated by the detector with the modulation frequencies" means that the above-mentioned frequency components may be evaluated to determine whether at least one condition is fulfilled or not. Thus, and as will be outlined in further detail below, the frequency components may be compared with one or more thresholds and/or with one or more tolerance ranges and/or with one or more conditions.

The ambient light fault detecting step may be performed before performing steps a)-e) (e.g., before applying the body fluid sample to the test carrier). Thus, steps may be performed without inserting a test carrier into the analytical device, such as by leaving a receptacle of the analytical device empty. Specifically, the ambient light fault detecting may be performed without a test carrier, such as without a test strip and/or without a test tape. Alternatively, a test carrier may be inserted into the analytical device, such as into at least one receptacle of the analytical device, and the ambient light fault detecting step may include at least one step of inserting the test carrier into the analytical device. Thus, the ambient light fault detecting optionally may take place in a realistic environment, with the test carrier inserted into the analytical device.

The ambient light fault detecting may be performed without using a light source of the analytical device, such as by detecting the ambient light only. Alternatively, the ambient light fault detecting may be performed with additionally using at least one light source. Thus, in case no test carrier is inserted into the analytical device, the at least one light source may illuminate at least one empty receptacle of the analytical device and/or may illuminate at least one spot or region within the analytical device that normally is occupied by the test carrier and/or a part thereof, such as a test field of the test carrier. Thus, the ambient light fault detecting may further imply an illumination, such as an illumination of the analytical device and/or a part thereof by using at least one light source. Consequently, the at least one detector signal generated by the detector may contain at least one part due to the ambient light and at least one part due to light generated by at least one light source of the analytical device.

If at least one test carrier is inserted into the analytical device for the purpose of the ambient light fault detecting and/or during the ambient light fault detecting, the process itself may further imply applying the body fluid sample to the test carrier. In the latter case, the ambient light fault detecting may be performed before applying the body fluid sample to the test carrier (e.g., before detecting the at least one detector signal for the purpose of ambient light fault detecting and/or before the light source is turned on and/or after the light source is turned on). Other options are feasible.

The ambient light fault detecting by comparing the at least one detector signal generated by the detector with the modulation frequencies may further imply a comparison, such as a mathematical comparison, of the frequency components of the at least one detector signal at the modulation frequencies with one or more thresholds and/or conditions and/or tolerance ranges. For this purpose, the frequency components of the at least one detector signal may, each by itself or in a combined fashion, as raw values or after performing one or more preprocessing steps such as filtering or normalization, be compared with one or more thresholds and/or conditions and/or tolerance ranges. For example, two or more of the frequency components of the at least one detector signal, as raw signals or after performing one or more preprocessing steps, be combined by using a quotient and/or a difference between two or more of the frequency components, and the result of this mathematical operation may be compared with one or more thresholds and/or conditions and/or tolerance ranges. The ambient light fault detection may be dependent on the result of this comparison. Thus, for example, in case one or more thresholds are exceeded and/or in case the result is found to be outside one or more tolerance ranges and/or in case one or more fault conditions are found to be fulfilled, a fault due to the ambient light may be detected, and, optionally, one or more appropriate actions may be taken automatically such as, for example, providing a warning and/or preventing further measurement. Additionally or alternatively, in case the at least one detector signal, one or more of a plurality of detector signals or at least one signal component of the at least one detector signal are found to be faulty, such as due to disturbances by ambient light, the respective faulty measurement signal or measurement signal component or the respective modulation frequency may be excluded when determining the analyte concentration. Thus, for example, the ambient light fault detecting may determine if one or more of the at least two modulation frequencies are such that demodulated detector signals for the respective at least one modulation frequencies are faulty and may exclude the respective at least one modulation frequency, which may be denoted as a "faulty modulation frequency" when determining the analyte concentration. Consequently, the faulty modulation frequency may be replaced by another modulation frequency when determining the analyte concentration. Additionally or alternatively, the at least one demodulated detector signal for the faulty modulation frequency, which may also be referred to as a "faulty demodulated detector signal," may be excluded from further evaluation and/or may be used with a lower weighting factor as compared to other demodulated detector signals. The demodulated detector signals may be used for determining an average value of the analyte concentration, such as a weighted average value, specifically a sliding average or a weighted sliding average. The averaging may take place before, during or after determining the analyte concentration. Thus, determining of the analyte concentration may be performed on the basis of one, more than one or all of the demodulated detector signals, such as by using a common correlation between the demodulated detector signals as input variables and the analyte concentration as output variables and/or by independently determining the analyte concentration by independently using demodulated detector signals as input variables and, subsequently, combining the independent results such as by determining a mean or average value or a weighted average value. Therein, in case one or more demodulated detector signals are determined as faulty demodulated detector signals during the ambient light fault detection, the one or more faulty demodulated detector signals may be excluded from the determination of the analyte concentration and/or may be used at a lower weight, such as by using lower weighting factors in the weighted average as compared to non-faulty demodulated detector signals.

The test carrier may be inserted into the receptacle of the analytical device. The test carrier, and/or the analytical device, and/or the light source, and/or the detector may be identical to the devices used in steps a)-e). Additionally or alternatively, however, at least one additional light source and/or at least one additional detector is dedicated to the ambient light fault detecting step. For a description of possible embodiments and definitions of these devices, reference can be made to the above-mentioned devices used in steps a)-e) and the above-mentioned analytical device. In general, other configurations of these devices may be possible.

As used herein, "ambient light" means light emitted by arbitrary light sources that are present when performing the methods herein (e.g., sun light, light of artificial light sources). The ambient light fault detecting may be performed, such as before performing steps a)-e), to determine the contribution of one or more possible modulation frequencies within the ambient light.

In this manner, the detector may receive the ambient light and may generate at least one detector signal. The at least one detector signal generated by the detector may be evaluated with respect to the contribution of one or more possible modulation frequencies within the ambient light. The evaluation may include comparing the at least one detector signal to the at least one modulation frequency and/or a set of modulation frequencies, which may be used for modulating the light source. In case the ambient light shows contributions of at least one modulation frequencies, which may be used for modulating the light source, the at least one modulation frequency may not be considered for the evaluation of the analyte concentration and/or the set of frequencies may be changed.

As outlined above, step d) implies determining the analyte concentration by evaluating the at least one detector signal generated by the detector. As used herein, "evaluating the at least one detector signal" means an arbitrary algorithm for deriving the analyte concentration from the at least one detector signal. The algorithm may be or may include an analytical algorithm such as an evaluation function. Additionally or alternatively, any other type of algorithm may be used, such as a lookup table or any other algorithm adapted to assign a specific value of the detector signal the analyte concentration. These algorithms generally are well known in the art. For example, an end value of a measurement curve including a sequence of detector signals may be used as a characteristic value, and the analyte concentration may be derived thereof. Thus, for example, the algorithms as disclosed in EP Patent No. 0 821 234 and in US Patent Application Publication No. 2002/0146835 may be used, in which the measurement curve directly or indirectly is compared with one or more thresholds. Specifically, EP Patent No. 0 821 234 discloses methods in which a slope of the measurement curve is determined by deriving difference values of colors and comparing these difference values with a predetermined threshold. Thereby, an end point of the detection reaction may be determined. Similarly, US Patent Application Publication No. 2002/0146835 discloses that an end point is determined by calculating an intermediate analyte level of the testing element at predetermined intervals and calculating a ratio value corresponding to the (n)th measurement to an (n−5)th measurement. When two consecutive ratio values are less than or equal to a predetermined value, the end point is deemed to be reached, and the final analyte concentration can be determined.

Further, several evaluation algorithms using one or more fitting algorithms are known in the art, in which the measurement curve comprising the detector signals is analyzed by using one or more fit functions. Thus, for example, Int'l Patent Application Publication No. WO 2011/061257 discloses methods and devices for analyzing body fluids in which a photometric measurement curve is measured. A transmission behavior of an optical transmission system is controlled by detecting measured values at two different measurement wavelengths. Further, fit functions are generated for the two measurement curves, and, by extrapolating fit curves, an offset of the measurement values is determined. Likewise, US Patent Application Publication No. 2008/0087819 discloses methods of analyzing fluid samples in which, again, two different wavelengths are used for deriving two measurement curves. The measurement curves are fitted by using an exponential rise with a subsequent exponential fall, by performing an appropriate fit algorithm having two different types of temporal constants.

Int'l Patent Application Publication No. WO 2001/025760 discloses timing-independent methods of determining a proper time for measurement of a reaction between a sample fluid and a reagent on an analyte strip. Therein, a measurement curve of a characteristic of a matrix, to which sample fluid is applied, is periodically measured both before and after sample fluid application. Subsequently, a transformation is made of this measurement curve into a function which is independent in time or at most various linearly in time. The second derivative of the transformed function is then analyzed to determine when the second derivative falls below a predetermined threshold. At this point in time, the transformed function will yield the analyte concentration in the sample fluid. Likewise, EP Patent Application Publication No. 1 413 883 discloses methods of reducing analysis time of end point-type reaction profiles. For this purpose, a detection reaction is initiated, obtaining at least three measurements, at three different points in time, of a value or level of an observable associated with the detection reaction. Subsequently, an end point value for the observable is estimated from the measurements, by using an appropriate fit function. Moreover, Int'l Patent Application Publication No. WO 2006/138226 discloses an arrangement and an algorithm for calculating an analyte concentration in a fluid sample. Therein, a color change rate of a test chemical is detected, and a hematocrit is derived from the color change rate. An appropriate correction factor indicative of the hematocrit is used for correcting a glucose concentration.

These algorithms and/or any other evaluation algorithm known to one of skill in the art may be used for performing step d), where, in certain embodiments, only non-faulty detector signals are used for determining the analyte concentration.

Step d) further may be performed by using a data processing device and/or computer. For example, the fault detecting may be performed by using a data processing device and/or computer when comparing of the demodulated detector signals.

In addition, it may be possible to store information of fault detecting for certain frequencies and/or reoccurring fault detections for certain frequencies. Thus, the methods may imply storing information on a previous fault detecting in at least one data memory, for use in future measurements. For example, information on one or more modulation frequencies that are known to be faulty and/or that are known to be non-faulty may be stored in at least one data memory. Thus, it may be possible to start the measurement with non-susceptible or non-faulty frequencies. The methods may be performed such that, automatically or by manual adjustment by a user, one or more modulation frequencies are chosen that are known to be non-faulty, such as from previous measurements. Thus, analytical devices performing the methods described herein may be adapted to offer two or more modulation frequencies to a user and/or may be adapted to automatically choose, such as without the need of a user input, two or more reliable modulation frequencies, which are known to be non-faulty, at least from previous measurements.

In certain instances, the methods further may include one or more or even all of the following steps, which may be performed before performing step a) (i.e., before applying the body fluid sample to the test carrier):

i. inserting the test carrier into an analytical device;
ii. initiating the fault detecting; and
iii. acquiring the dry empty value.

As outlined above with regard to steps a)-e), steps i.-iii. may be performed in the given order and/or in any other feasible order, as will be evident to one of skill in the art. Further, one or more or even all of these additional steps may be combined with one or more of steps a)-e).

For further details of the analytical device, reference may be made to the disclosure of the second aspect as given below.

The methods herein allow fault detecting basically at any reasonable time of the photometric measurement, as will be evident to one of skill in the art. Further, it may be possible to avoid faulty or inaccurate measurement values caused by disturbances of ambient light by changing from the used, susceptible frequencies to frequencies, which are not susceptible. This is achieved on the one hand by comparing the demodulated detector signals at a very early stage of the measurement (e.g., during the determination of the dry empty value) instead of comparing the evaluated value of the analyte concentration. Moreover, this is achieved by using more than one set of modulation frequencies. Thus, it is possible to change the set frequencies in case of fault detecting. In general, the amount of frequency changes is not limited. However, the settling time of the used measurement devices may have to be considered.

In addition, the described fault detecting at the very early stage of the measurement provides the possibility to secure the robustness of the determined analyte concentration by detecting disturbances before applying the body fluid sample to the test carrier. A pre-selection of the set of frequencies may be possible by performing one or more frequency changes and/or one or more fault detectings before applying the body fluid sample to the test carrier. Thus, the set of frequencies, which has the lowest susceptibility, can be preselected.

For example, the methods may be performed with the following two modulation frequencies of 1,488 kHz and 1,587 kHz. If the demodulated detector signal generated when determining the dry empty value for this set of frequencies shows discrepancies above a certain threshold value, this pair may be detected as faulty and may be rejected. In this case, the set of frequencies may be changed to another set of frequencies (e.g., 1,302 kHz and 1,389 kHz). If again this set of frequencies shows discrepancies above a certain threshold, this pair may be detected as faulty and may be rejected too. Again the second set of frequencies may be changed to another set of frequencies (e.g., 1,645 kHz and 1,754 kHz). In case the third set of frequencies is not detected faulty, the sample is applied to the carrier and measurement of the analyte concentration of the analyte will start.

Additionally or alternatively to comparing the demodulated detector signals with one threshold value, two or more threshold values may be established. The at least one threshold value may be or may include at least one predetermined threshold value and/or may be or may include at least one adjustable threshold value, which may be adjustable manually and/or automatically. For example, one narrow threshold value (e.g., a deviation of the demodulated detector signals of about 0.5%) and one wider threshold value (e.g., a deviation of the demodulated detector signals of about 1-2%). In case the deviation of the demodulated detector signals lies within the narrow threshold range, a warning may be generated to display to a user that the measurement is questionable. Instead, if the deviation of the demodulated detector signals lies within the wider threshold range, a change of the susceptible frequency or an abortion of the measurement may be performed.

In some instances, more than two frequencies may be used for the modulation of the light source. For example, three, four or more than four frequencies may be used for the modulation of the light source (e.g., fi, fii, fiii). Here, the three demodulated detector signals for the three modulation frequencies may be generated and may be compared. Hence, if only one of the frequencies is susceptible, it may be possible to use only non-faulty demodulated detector signals for the evaluation of the analyte concentration. A resulting detector signal may be determined as mean value of the non-faulty demodulated detector signals. For example, if frequency fi is susceptible and fii and fiii are not, it may be possible to consider only the frequencies fii and fiii for evaluating the analyte concentration. For example, the methods may be aborted only if all of the three demodulated detector signals show different values. Thus, it may be possible to determine the analyte concentration even in case of fault detection for one of the frequencies without changing the whole set of frequencies.

For example, and in some instances, two LEDs may be used as light sources. The signal of one of the light sources may be modulated with three frequencies (e.g., f1a=977 Hz, f1b=1465 Hz, and f1c=1953 Hz). The signal of the other light source may be modulated with three other frequencies (e.g., f2a=1172 Hz, f2b=1563 Hz, and f2c=2344 Hz). During the fault detecting, and in a first step, the demodulated detector signals of f1a and f1b may be compared. In a second step, these demodulated detector signals may be compared with the demodulated detector signal of f1c. The mean detector output signal may be evaluated only from equal values, where equal indicates equal within a certain threshold. At least two values may be needed when evaluating the mean detector output signal. If all demodulated detector signals differ more than the predefined threshold value, an error value may be generated and a change to other than the susceptible frequencies may be performed. An equal method may be applied to frequencies of the second light source. The two determined mean values may be further evaluated to determine the analyte concentration. At this late stage of the measurement, it may be further possible to compare the two determined analyte concentrations. If the two measurement results are not equal a warning and/or an error value may be issued.

Computer Programs, Computers and Data Carriers

In view of the above-described methods, this disclosure also provides computer programs including computer-executable instructions for performing the methods herein and/or parts thereof, in one or more of the embodiments enclosed herein, when the program is executed on a processor residing within an analytical device or on a computer or computer network. Specifically, the computer program may be stored on a computer-readable data carrier (e.g., on a ROM such as a Flash-ROM, such as a computer-readable data carrier and/or a ROM (such as a Flash-ROM)) of the test carrier. Thus, specifically, one or more than one, or even all of steps a)-d) as indicated above may be performed by using a processor residing within the analytical device, a computer, or a computer network, especially by using a computer program. In particular, one or more of determining the analyte concentration as disclosed in step d), demodulating the at least one detector signal, and fault detecting may be performed by using a processor residing within the analytical device, a computer, or a computer network.

In addition, computer program products are provided, where such products have program code means to perform the methods herein and/or parts thereof, in one or more of the embodiments enclosed herein when the program is executed on a processor residing within the analytical device, on a computer, or on a computer network. Specifically, the program code means may be stored on a computer-readable data carrier.

Further provided are data carriers having a data structure stored thereon, which, after loading into a data storage residing within the analytical device, a computer, or a computer network, such as into a working memory or main memory of the computer or computer network, may execute the methods herein and/or parts thereof, according to one or more of the embodiments disclosed herein.

This disclosure further proposes a computer program product with program code means stored on a machine-readable carrier, in order to perform the method and/or parts thereof, according to one or more of the embodiments disclosed herein, when the program is executed on a processor residing within the analytical device, on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, modulated data signals are provided that include instructions readable by a processor residing within the analytical device, a computer system, or a computer network, for performing the methods herein and/or parts thereof, according to one or more of the embodiments disclosed herein.

In connection with the computer-implemented aspects of this disclosure, one or more of the steps or even all of the steps of the methods herein may be performed by using a processor residing within the analytical device, a computer, or a computer network. Thus, any of the steps including provision and/or manipulation of data may be performed by using a processor residing within the analytical device, a computer or, a computer network. Generally, these steps may include any of the steps, typically except for steps requiring manual work, such as providing the samples and/or certain aspects of performing the actual measurements.

In addition to the above-described analytical devices, analytical systems and methods, the present disclosure provides:

An analytical device, a computer, or computer network including at least one processor, where the processor is adapted/configured to perform the methods herein and/or parts thereof.

A computer-loadable data structure adapted/configured to perform the methods herein and/or parts thereof while the data structure is being executed on a computer.

A computer program adapted/configured to perform the methods herein and/or parts thereof while the program is being executed on a processor residing within an analytical device as described herein or on a computer.

A computer program including program means for performing the methods herein and/or parts thereof while the computer program is being executed on a processor residing within an analytical device as described herein, on a computer, or on a computer network.

A computer program including program means according to the preceding embodiment, where the program means are stored on a storage medium readable to a computer.

A storage medium, where a data structure is stored on the storage medium and where the data structure is adapted/configured to perform the methods herein and/or parts thereof after having been loaded into a main and/or working storage of an analytical device as described herein, a computer, or a computer network.

A computer program product having program code means, where the program code means can be stored or are stored on a storage medium, for performing the methods herein and/or parts thereof if the program code means are executed on an analytical device as described herein, on a computer, or on a computer network.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

LISTING OF REFERENCE NUMBERS 110 analytical system
112 body fluid
114 analytical device
116 test carrier
118 substrate
120 test chemical
122 receptacle
124 modulation devices
125 signal source
126 mixer unit
127 light source
128 first light source
130 second light source
132 detector
133 detector signal
134 demodulation device
136 multiplication device
138 low-pass filter
139 demodulated detector signals
140 lock-in amplifier
142 band pass filter
144 fault detection device
146 comparison procedure
148 evaluation unit
150 modulation frequency
152 modulation frequency
154 modulation frequency
156 modulation frequency
158 modulation frequency
160 modulation frequency

The invention claimed is:

1. A method of determining at least one analyte concentration in a body fluid sample, the method comprising the steps of:
   a). applying the body fluid sample to a test carrier;
   b). illuminating the test carrier with at least one light source, the at least one first light source comprising at least one first light source being modulated by at least two modulation frequencies and at least one second light source being modulated by at least two modulation frequencies being different from the at least two modulation frequencies by which the first light source is modulated, wherein the at least one light source is modulated by using at least two different modulation frequencies;
   c). receiving light remitted by the test carrier with at least one detector;
   d). determining an analyte concentration by evaluating at least one detector signal generated by the at least one detector, wherein the at least one detector signal is demodulated with the at least two different modulation frequencies to generate at least two demodulated detector signals, each demodulated detector signal corresponding to one of the at least two modulation frequencies; and
   e). detecting a fault by comparing the at least two demodulated detector signals.

2. The method of claim 1, wherein step e) is an online fault detection performed permanently or repeatedly.

3. The method of claim 1, wherein the at least one light source is modulated by using at least three modulation frequencies.

4. The method of claim 1, wherein step e) further comprises detecting faulty demodulated detector signals.

5. The method of claim 4, wherein step e) further comprises rejecting faulty demodulated detector signals and using only non-faulty demodulated detector signals for determining the at least one analyte concentration in the body fluid sample.

6. The method of claim 5, wherein at least one faulty demodulated detector signal is used for determining the at least one analyte concentration, and wherein a degree of faultiness is taken into account.

7. The method of claim 1, wherein the at least one light source comprises at least one first light source being modulated by at least two modulation frequencies and at least one second light source being modulated by at least two modulation frequencies being different from the at least two modulation frequencies by which the first light source is modulated.

8. The method of claim 7, wherein at least two demodulated detector signals are generated for the modulation frequencies by which the first light source is modulated, and wherein at least two demodulated detector signals are generated for the modulation frequencies by which the second light source is modulated.

9. The method of claim 8, wherein step e) is performed both for the at least two demodulated detector signals for the at least two different modulation frequencies by which the first light source is modulated and for the at least two demodulated detector signals for the modulation frequencies by which the second light source is modulated.

10. The method of claim 1, wherein step e) is performed at least once before step a).

11. The method of claim 10, further comprising the step of:
    determining at least one dry empty value by evaluating the at least one detector signal generated by the at least one detector before applying the body fluid sample to the test carrier.

12. The method of claim 1, further comprising the step of:
    verifying at least one position of the test carrier, wherein the verifying step comprises the steps of:
    i) inserting the test carrier into an analytical device;
    ii) illuminating the test carrier by the at least one light source;
    iii) receiving light remitted by the test carrier by using the at least one detector; and
    iv) determining at least one position of the test carrier within the analytical device by evaluating at least one detector signal generated by the at least one detector, wherein the at least one position comprises at least one of a location or an orientation of the test carrier.

13. The method of claim 1, further comprising the step of:
    detecting at least one ambient light fault, wherein the ambient light fault detecting step comprises the steps of:
    I. receiving ambient light by using the at least one detector;
    II. evaluating at least one detector signal generated by the at least one detector; and III. performing an ambient light fault detection by comparing the at least one detector signal generated by the at least one detector with the at least two different modulation frequencies.

14. The method of claim 1, wherein the demodulation comprises independently multiplying the at least one detector signal with the at least two different modulation frequencies and filtering the results by using low pass filters.

15. The method of claim 14, wherein the demodulation, before multiplying the at least one detector signal with the at least two different modulation frequencies, comprises filtering the at least one detector signal by using at least one band pass filter.

16. The method of claim 1, further comprising at least one of the following steps:
   inserting the test carrier into an analytical device;
   initiating the fault detecting; and
   acquiring a dry empty value.

17. An analytical device for determining at least one analyte concentration in a body fluid, the analytical device comprising:
   at least one receptacle for receiving at least one test carrier, wherein at least one body fluid sample is applicable to the at least one test carrier;
   at least one light source configured for illuminating the at least one test carrier, the at least one light source comprising at least one first light source configured to be modulated by at least two modulation frequencies and at least one second light source configured to be modulated by at least two modulation frequencies being different from the at least two modulation frequencies by which the first light source is modulated;
   at least one detector configured for receiving light remitted by the at least one test carrier;
   at least one evaluation unit configured for determining the at least one analyte concentration by evaluating at least one detector signal generated by the at least one detector;
   at least one modulation device configured for modulating the at least one light source by using at least two different modulation frequencies;
   at least one demodulation device configured for the demodulating the at least one detector signal with the at least two modulation frequencies to generate at least two demodulated detector signals, each demodulated detector signal corresponding to one of the at least two different modulation frequencies; and
   at least one fault detection device configured for performing a fault detection based on a comparison of the at least two demodulated detector signals.

18. An analytical system for determining at least one analyte concentration in a body fluid sample, the analytical system comprising:
   the analytical device of claim 17; and
   at least one test carrier.

* * * * *